US00PP18406P2

(12) United States Plant Patent
Verwer

(10) Patent No.: US PP18,406 P2
(45) Date of Patent: Jan. 8, 2008

(54) ***DAHLIA* PLANT NAMED 'KARMA IRENE'**

(50) Latin Name: *Dahlia hybrida*
Varietal Denomination: Karma Irene

(75) Inventor: Aad W. M. Verwer, Lisse (NL)

(73) Assignee: Verwer Dahlias B.V., Lisse (NL)

( * ) Notice: Subject to any disclaimer, the term of this patent is extended or adjusted under 35 U.S.C. 154(b) by 0 days.

(21) Appl. No.: 11/524,406

(22) Filed: Sep. 20, 2006

(51) Int. Cl.
*A01H 5/00* (2006.01)

(52) U.S. Cl. ..... Plt./321

(58) Field of Classification Search ..... Plt./321
See application file for complete search history.

*Primary Examiner*—Kent Bell
(74) *Attorney, Agent, or Firm*—C. A. Whealy

(57) ABSTRACT

A new and distinct cultivar of *Dahlia* plant named 'Karma Irene', characterized by its upright and somewhat outwardly spreading plant habit; early flowering habit; strong and erect peduncles; decorative-type inflorescence form; large inflorescences with red orange-colored ray florets; and good garden performance and postproduction longevity.

2 Drawing Sheets

Botanical designation: *Dahlia hybrida.*
Cultivar denomination: 'Karma Irene'.

BACKGROUND OF THE INVENTION

The present invention relates to a new and distinct cultivar of *Dahlia* plant, botanically known as *Dahlia hybrida,* and hereinafter referred to by the name 'Karma Irene'.

The new *Dahlia* is a product of a planned breeding program conducted by the Inventor in Lisse, The Netherlands. The objective of the breeding program is to create new cut flower *Dahlia* cultivars that have a freely flowering habit, decorative inflorescence form, attractive ray floret coloration, and good postproduction longevity.

The new *Dahlia* originated from an open-pollination in Lisse, The Netherlands during 2000, of the *Dahlia hybrida* cultivar Karma Fuschsiana, not patented, as the female, or seed, parent with an unknown selection of *Dahlia hybrida,* as the male, or pollen, parent. The new *Dahlia* was discovered and selected by the Inventor as a single flowering plant within the progeny of the stated open-pollination in a controlled environment in Lisse, The Netherlands during 2001.

Asexual reproduction of the new *Dahlia* by cuttings since the spring of 2002 in a controlled environment in Lisse, The Netherlands, has shown that the unique features of this new *Dahlia* are stable and reproduced true to type in successive generations.

SUMMARY OF THE INVENTION

The cultivar Karma Irene has not been observed under all possible environmental conditions. The phenotype may vary somewhat with variations in environment such as temperature and light intensity, without, however, any variance in genotype.

The following traits have been repeatedly observed and are determined to be the unique characteristics of 'Karma Irene'. These characteristics in combination distinguish 'Karma Irene' as a new and distinct cultivar of *Dahlia:*

1. Upright and somewhat outwardly spreading plant habit.
2. Freely flowering habit.
3. Strong and erect peduncles.
4. Decorative-type inflorescence form.
5. Large inflorescences with red orange-colored ray florets.
6. Good garden performance and postproduction longevity.

Compared to plants of the female parent, the cultivar Karma Fuchsiana, plants of the new *Dahlia* differ in the following characteristics:

1. Plants of the new *Dahlia* are larger than plants of the cultivar Karma Fuchsiana.
2. Plants of the new *Dahlia* have lighter green-colored leaves than plants of the cultivar Karma Fuchsiana.
3. Plants of the new *Dahlia* have larger inflorescences than plants of the cultivar Karma Fuchsiana.
4. Plants of the new *Dahlia* have broader ray florets than plants of the cultivar Karma Fuchsiana.
5. Plants of the new *Dahlia* and the cultivar Karma Fuchsiana differ in ray floret color as plants of the cultivar Karma Fuchsiana have orange and red purple bi-colored ray florets.

Plants of the new *Dahlia* can be compared to plants of the *Dahlia* cultivar Arabian Night, not patented. In side-by-side comparisons conducted in Lisse, The Netherlands, plans of the new *Dahlia* differed from plants of the cultivar Arabian Night in the following characteristics:

1. Plants of the new *Dahlia* were larger and stronger than plants of the cultivar Arabian Night.
2. Inflorescences of plants of the new *Dahlia* were longer lasting than inflorescences of plants of the cultivar Arabian Night.
3. Ray florets of plants of the new *Dahlia* were lighter in color than ray florets of plants of the cultivar Arabian Night.

BRIEF DESCRIPTION OF THE PHOTOGRAPHS

The accompanying photographs illustrate the overall appearance of the new *Dahlia*. The photographs show the colors as true as it is reasonably possible to obtain in colored reproductions of this type. Colors in the photographs may differ slightly from the color values cited in the detailed botanical description which accurately describe the colors of the new *Dahlia*.

The photograph on the first sheet comprises a side perspective view of typical flowering plants of 'Karma Irene' grown in an outdoor nursery.

The photograph on the second sheet is a close-up view of a typical inflorescence of 'Karma Irene'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Lisse, The Netherlands during the summer in an outdoor nursery and under conditions and practices which approximate those generally used in commercial *Dahlia* production. During the production of the plants, day temperatures ranged from 15° C. to 30° C. and night temperatures ranged from 10° C. to 20° C. Plants were pinched one time about three to four weeks after planting. Measurements and numerical values represent averages for typical flowering plants. Plants were about four months old when the photographs and description were taken.

Botanical classification: *Dahlia hybrida* cultivar Karma Irene.

Parentage:

*Female, or seed, parent.*—*Dahlia hybrida* cultivar Karma Fuchsiana, not patented.

*Male, or pollen, parent.*—Unknown selection of *Dahlia hybrida,* not patented.

Propagation:

*Type.*—By cuttings.

*Time to initiate roots, summer.*—About ten days at temperatures of about 18° C.

*Time to initiate roots, winter.*—About twelve days at temperatures of about 18° C.

*Time to produce a rooted young plant, summer.*—About 24 days at temperatures of about 18° C.

*Time to produce a rooted young plant, winter.*—About 27 days at temperatures of about 18° C. to 20° C.

*Root description.*—Fine to fleshy; tuber development has not been observed.

*Rooting habit.*—Freely branching; dense.

Plant description:

*Plant form/growth habit.*—Upright to somewhat outwardly spreading; inverted triangle plant form. Freely basal branching with about four lateral branches and inflorescences held above the foliage on strong peduncles; bushy and dense. Vigorous growth habit.

*Plant height.*—About 100 cm.

*Plant diameter or spread.*—About 45 cm.

*Lateral branches.*—Length: about 20 to 25 cm. Diameter: Towards the base, about 5 cm; towards the apex, about 3 mm. Internode length: About 7 cm to 15 cm. Aspect: Erect to somewhat outwardly spreading. Strength: Strong. Texture: Smooth, glabrous. Color: 153A tinted with 183B.

Foliage description:

*Arrangement.*—Leaves opposite; leaves may be single or compound with three or five leaflets.

*Shape.*—Ovate.

*Apex.*—Acuminate.

*Base.*—Attenuate.

*Margin.*—Serrate and divided; sinuses divergent.

*Length.*—Single leaves: About 10 cm. Compound leaves with three leaflets: About 15 cm. Compound leaves with five leaflets: About 23 cm.

*Width.*—Single leaves: About 5 cm. Compound leaves with three leaflets: About 9 cm. Compound leaves with five leaflets: About 13 cm.

*Venation pattern.*—Pinnate.

*Texture, upper and lower surfaces.*—Smooth, glabrous.

*Color.*—Developing and fully expanded foliage, upper surface: 137A; venation, 148C. Developing and fully expanded foliage, lower surface: 147B; venation, 137B.

*Petiole length.*—Single leaves: About 2 cm. Compound leaves with three leaflets: About 3 cm. Compound leaves with five leaflets: About 6 cm.

*Petiole diameter.*—Single leaves: about 3 mm. Compound leaves with three leaflets. About 5 mm. Compound leaves with five leaflets. About 7 mm.

*Petiole texture, upper and lower surfaces.*—Smooth, glabrous.

*Petiole color, upper and lower surfaces.*—1D.

Inflorescence description:

*Appearance.*—Rotate single inflorescence form with ray and disc florets. Inflorescences positioned above the foliage on strong peduncles. Inflorescences face upright to slightly outwardly. Freely flowering habit; about 70 inflorescences develop per plant. Inflorescences persistent. Inflorescences not fragrant.

*Time to flower.*—Plants flower continuously during the summer and autumn in The Netherlands.

*Post-production longevity.*—Good postproduction longevity; inflorescences maintain good substance for about 22 days on the plant and for about ten days as a cut flower.

*Inflorescence bud.*—Height: About 1.5 cm. Diameter: About 2.1 cm. Shape: Oblate. Color: 144A; towards the apex, 151C.

*Inflorescence size.*—Diameter: About 11 cm. Depth (height): About 5 cm. Disc diameter: About 1.6 cm. Receptacle height: About 2 cm. Receptacle diameter: About 2 cm.

*Ray florets.*—Length: About 4.4 cm. Width: About 2.1 cm. Shape: Ovate to elliptic. Apex: Slightly retuse or obtuse. Base: Attenuate. Aspect: Initially upright to roughly perpendicular to the peduncle to reflexed; flat or cupped. Texture, upper and lower surfaces: Smooth, glabrous; satiny. Number of ray florets per inflorescence: About 120 arranged in about 15 whorls. Color: When opening, upper surface: 42A; towards the margins, 45A. When opening, lower surface: 42A; longitudinal stripes. 15B. Fully opened, upper surface: Center, 34B; toward the apex, 42A; towards the base, 15B. Fully opened, lower surface: Center and towards the margins, 42B; longitudinal stripes and towards the base, 16B.

*Disc florets.*—Shape: Tubular; apex dentate. Length: About 7 mm. Diameter, apex: About 1 mm.

Diameter, base: About 1 mm. Number of disc florets per inflorescence: About 20. Color: Immature: 1B. Mature: Apex: 15A. Mid-section: 1B. Base: 1D.

*Phyllaries.*—Quantity per inflorescence: About six arranged in a single whorl. Length: About 2 cm. Width: About 1.4 cm. Shape: Ovate, broad. Apex: Obtuse. Base: Attenuate. Margin: Entire. Texture, upper and lower surfaces: Smooth, glabrous; satiny. Color, upper and lower surfaces: 144A.

*Peduncles.*—Length: Terminal peduncle: About 30 cm. Fourth peduncle: About 18 cm. Seventh peduncle: About 15 cm. Diameter: Towards the base, about 1.5 cm; towards the apex, about 4 mm. Strength: Strong. Aspect: Erect to about 10° from vertical. Texture: Smooth, glabrous. Color: 183B.

*Reproductive organs.*—Androecium: Quantity per disc floret: Five. Anther shape: Linear. Anther length: About 1 mm. Anther color: 16B. Pollen amount: Scarce. Pollen color: 23A. Gynoecium: Quantity per ray or disc floret: One. Pistil length: About 3 mm. Stigma shape: Lanceolate. Stigma color: 1C. Style length: About 2 mm. Style color: 1D. Ovary color: 1A. Seeds: Seed development has not been observed.

Disease/pest resistance: Plants of the new *Dahlia* have not been shown to be resistant to pathogens and pests common to *Dahlia*.

Garden performance: Plants of the new *Dahlia* have exhibited good tolerance to rain and wind and have been observed to tolerate temperatures from about 0° C. to about 35° C.

It is claimed:

1. A new and distinct *Dahlia* plant named 'Karma Irene' as illustrated and described.

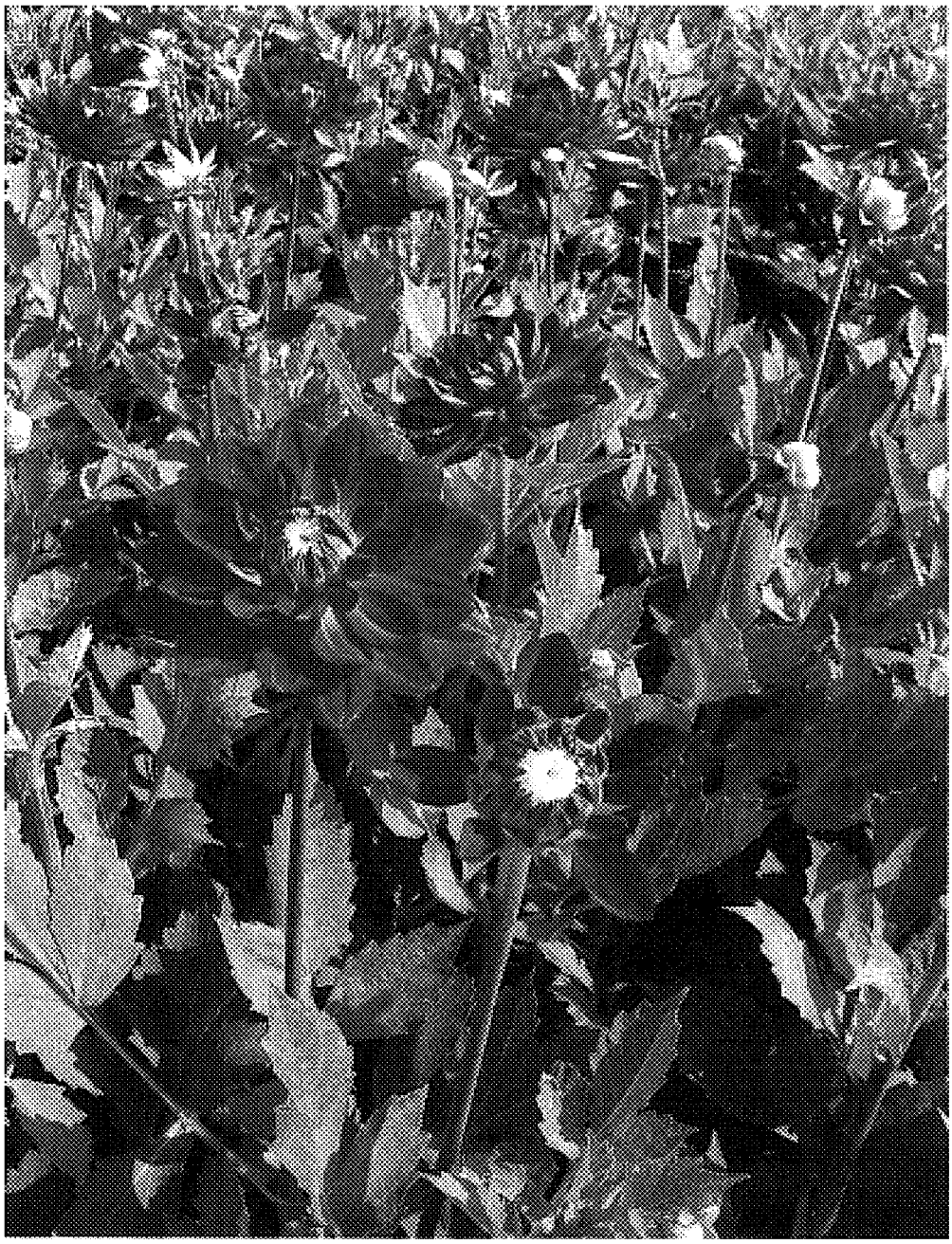

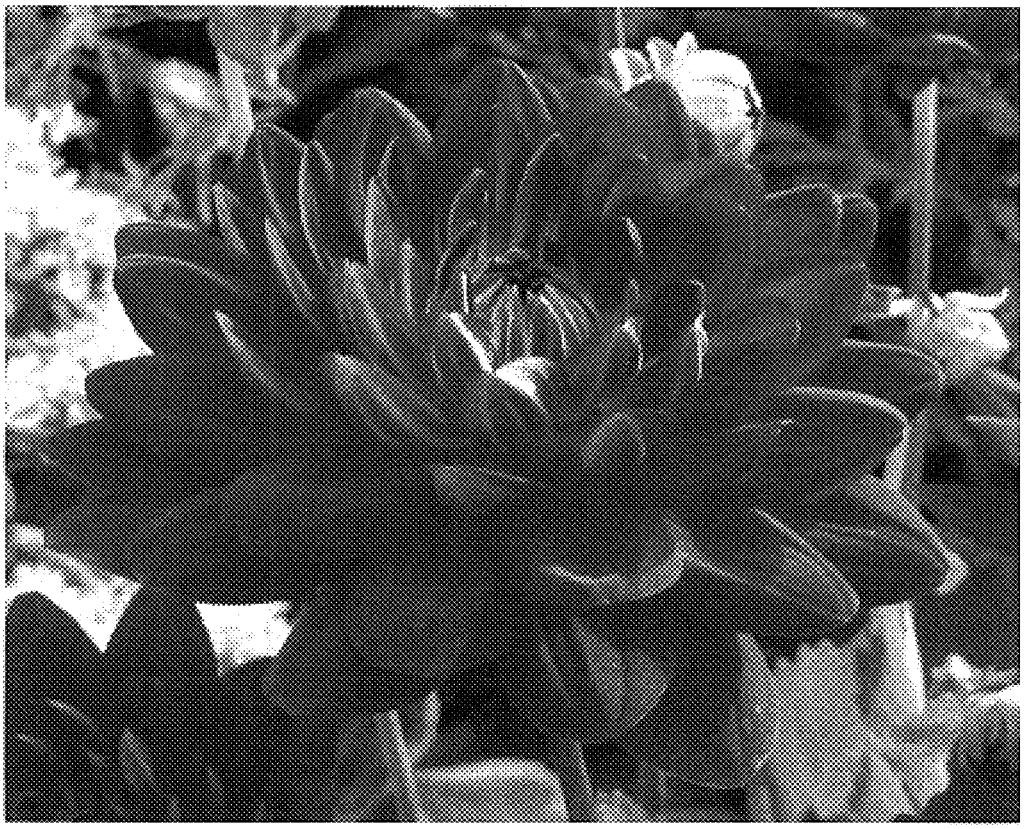

* * * * *